United States Patent
Lu et al.

(10) Patent No.: US 9,717,946 B2
(45) Date of Patent: Aug. 1, 2017

(54) SYSTEMS AND METHODS FOR TRAINING AND IMAGING AN ANIMAL IN AN AWAKEN STATE

(71) Applicant: The United States of America, as represented by the Secretary, Dept. of Health and Human Services, Washington, DC (US)

(72) Inventors: Hanbing Lu, Rockville, MD (US); Yihong Yang, Rockville, MD (US); Elliot A. Stein, Rockville, MD (US)

( * ) Notice: Subject to any disclaimer, the term of this patent is extended or adjusted under 35 U.S.C. 154(b) by 236 days.

(21) Appl. No.: 14/589,725

(22) Filed: Jan. 5, 2015

(65) Prior Publication Data

US 2016/0192891 A1 Jul. 7, 2016

(51) Int. Cl.
| | |
|---|---|
| *A61B 5/05* | (2006.01) |
| *A63B 22/02* | (2006.01) |
| *A61B 5/055* | (2006.01) |
| *A61B 6/04* | (2006.01) |
| *A61B 6/00* | (2006.01) |

(Continued)

(52) U.S. Cl.
CPC ............ *A63B 22/02* (2013.01); *A61B 5/0555* (2013.01); *A61B 6/0407* (2013.01); *A61B 6/508* (2013.01); *A63B 22/0221* (2015.10); *A63B 22/0242* (2013.01); *A63B 22/0257* (2013.01); *A61B 6/032* (2013.01); *A61B 6/037* (2013.01); *A61B 2503/40* (2013.01); *A61B 2503/42* (2013.01); *A63B 2071/0675* (2013.01); *A63B 2208/14* (2013.01); *A63B 2213/00* (2013.01); *A63B 2220/30* (2013.01); *A63B 2220/833* (2013.01); *A63B 2225/54* (2013.01); *A63B 2230/00* (2013.01)

(58) Field of Classification Search
CPC ....... A61B 5/0046; A61B 5/055; A61B 5/222; A61B 5/02; A61B 5/0044; A61B 5/0075; A61B 5/0077; A61B 5/7282; A61B 5/7267

See application file for complete search history.

(56) References Cited

U.S. PATENT DOCUMENTS

| | | | | |
|---|---|---|---|---|
| 2009/0259121 | A1* | 10/2009 | Simonetti | A61B 5/0046 600/410 |
| 2012/0059235 | A1* | 3/2012 | Davies | A01K 11/008 600/364 |
| 2016/0073614 | A1* | 3/2016 | Lampe | A01L 11/00 600/408 |

OTHER PUBLICATIONS

King, J.A., et al., "Procedure for minimizing stress for fMRI studies in conscious rats." J. Neurosci Methods, 2005; 148(2), pp. 154-160.
(Continued)

*Primary Examiner* — Joel Lamprecht
(74) *Attorney, Agent, or Firm* — Polsinelli PC

(57) ABSTRACT

Systems for training an animal, such as a rodent, to maintain its head substantially motionless during an imaging procedure using an imaging and training system are disclosed. In some embodiments, the imaging and training system includes a frame defining an enclosure for enclosing an animal therein during the imaging procedure. The frame includes a head post that is attached to the head of the animal and a treadmill having a plurality of rollers that the animal is in operative contact such that one or more of the plurality of wheels rotate when the animal is in a walking motion and stop rotating when the animal is in a substantially motionless state. This arrangement trains the animal to remain substantially motionless when disposed within an imaging apparatus.

15 Claims, 2 Drawing Sheets

(51) Int. Cl.
 A61B 6/03 (2006.01)
 A63B 71/06 (2006.01)

(56) References Cited

OTHER PUBLICATIONS

Martin, C., et al., "Haemodynamic and neural responses to hypercapnia in the awake rat." Eur. J. Neurosci., 2006, 24(9), pp. 2601-2610.
Desai, M., et al., "Mapping brain networks in awake mice using combined optical neural control and fMRI," J. Neurophysiol., 2011, 105(3), pp. 1393-1405.

* cited by examiner

SYSTEMS AND METHODS FOR TRAINING AND IMAGING AN ANIMAL IN AN AWAKEN STATE

FIELD

The present document generally relates to medical imaging of animals, and in particular to systems and methods for training and imaging an animal in an awaken state.

BACKGROUND

Animal imaging, using a Magnetic Resonance Imaging (MRI), Computer Tomography (CT), and Positron Emission Tomography (PET), plays an important role in basic neuroscience and drug discovery. Referring to FIG. 1, for example a conventional imaging apparatus 10, such as an MRI scanner, is illustrated. As shown, a typical MRI apparatus forms a strong magnetic field around the area to be imaged. In one embodiment, a conventional MRI apparatus 10 includes a patient table 14 configured to receive a patient 12 thereon in which the patient 14 is temporarily exposed to an oscillating magnetic field applied by a Radio Frequency (RF) coil 16 of the MRI apparatus 10 at the appropriate resonant frequency. The excited hydrogen atoms in the tissue of the patient 14 become excited by the oscillating magnetic field applied by the RF coil 16 and emit a radio frequency signal which is then detected and measured by a radio receiver coil. The radio receiver coil could be the same one as the RF coil 16 (but switched from RF transmitter mode to RF reception mode) or a separate RF receiver coil for better sensitivity. Typically, the radio frequency signal received by the radio receiver coil 16 can be made to encode position information by varying the main magnetic field using gradient coils 18, which are rapidly switched on and off to create the characteristic repetitive noises of an MRI scan. The contrast between different tissues is then determined by the rate at which excited atoms return to an equilibrium state.

A typical imaging session using the MRI apparatus 10 can take over 45 minutes and can last as long as several hours, depending on experimental protocols, during which the subject being imaged must remain still during the imaging procedure, otherwise imaging artifacts would occur. In particular, animals being imaged, such as rodents in an awaken state, are not readily compliant with the restricted movement required when being imaged.

Current techniques for imaging animals in an awaken state aim to train them to remain still for a prolonged period of time during imaging with the aid of a body restraint along with head fixation using a bite bar and/or ear bars or head mount. However, physically restraining the animal can induce stress, thereby resulting in unavoidable movement of the stressed animal in many cases.

Due to the limitations of imaging animals in an awaken state, a majority of animal imaging is conducted when the animal is under anesthesia. However, anesthetics compromise brain functions of the animal under anesthesia, while some anesthetics can directly interact with the pharmacological compounds being tested, thereby potentially skewing data being collected.

As such, there is a need for improvements in systems and methods for imaging of animals in an awaken state.

BRIEF DESCRIPTION OF THE DRAWINGS

Corresponding reference characters indicate corresponding elements among the view of the drawings. The headings used in the figures do not limit the scope of the claims.

DETAILED DESCRIPTION

Figure 1:
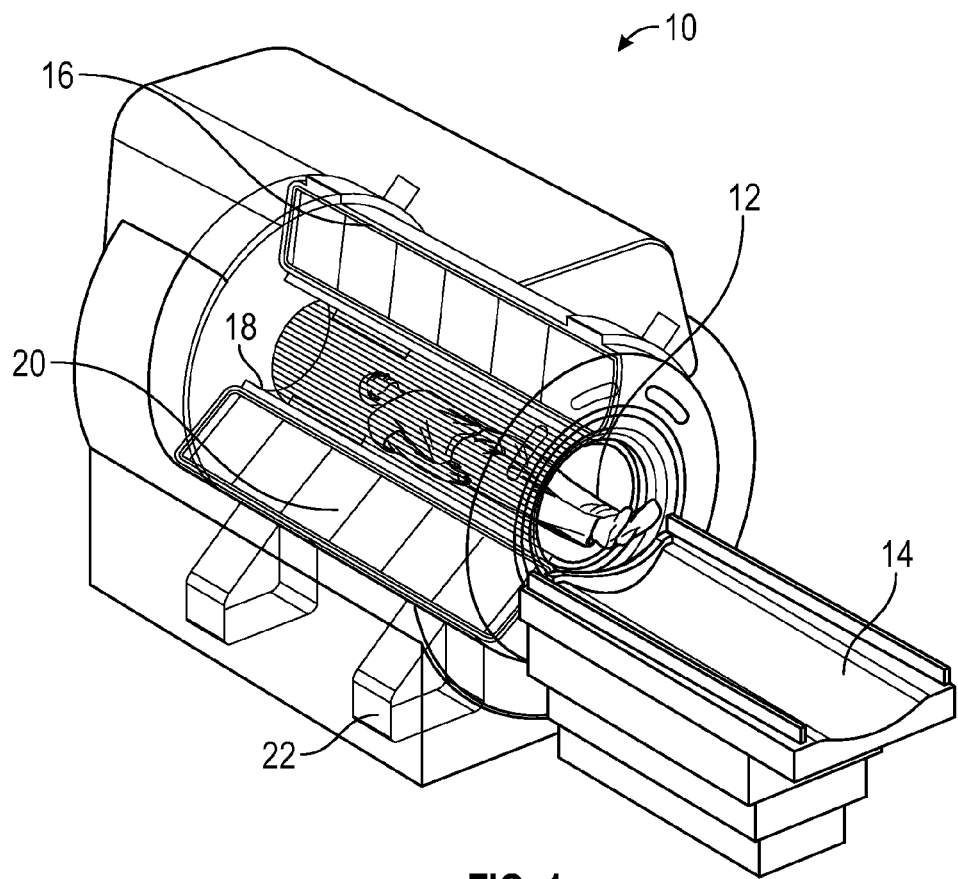
FIG. 1 is a perspective view of a conventional imaging apparatus used for imaging a mammalian subject.

Referring to the drawings, systems and methods for imaging and training an animal are illustrated and generally indicated as 100 in FIGS. 2-5. In some embodiments, the imaging and training system and method may be used with an imaging apparatus 114, such as the imaging apparatus 114 shown in FIG. 5, for example, a Magnetic Resonance Imaging (MRI) apparatus. In other embodiments, the imaging apparatuses 114 may be other types of medical imaging apparatus, such as Computer Tomography (CT) apparatus or Positron Emission Tomography (PET) apparatus. In one embodiment, the imaging apparatus 114 is used for neuroimaging of animals, and in particular to imaging the structure and function of the rodent brain.

Referring to FIGS. 2-5, various embodiments of a system and method for training and imaging a rodent to remain sufficiently still while in an awaken state during medical imaging are shown. In one embodiment, the imaging and training system 100 may include a frame 108 that forms an enclosure configured to confine a rodent therein. The frame 108 includes a treadmill 102 having a plurality of rollers 110 rotatably disposed along the lower portion of the treadmill 102. The plurality of rollers 110 may rotate either clockwise or counter counterclockwise without an electric motor or other driving means to cause rotation of the plurality of rollers 110.

Figure 2:
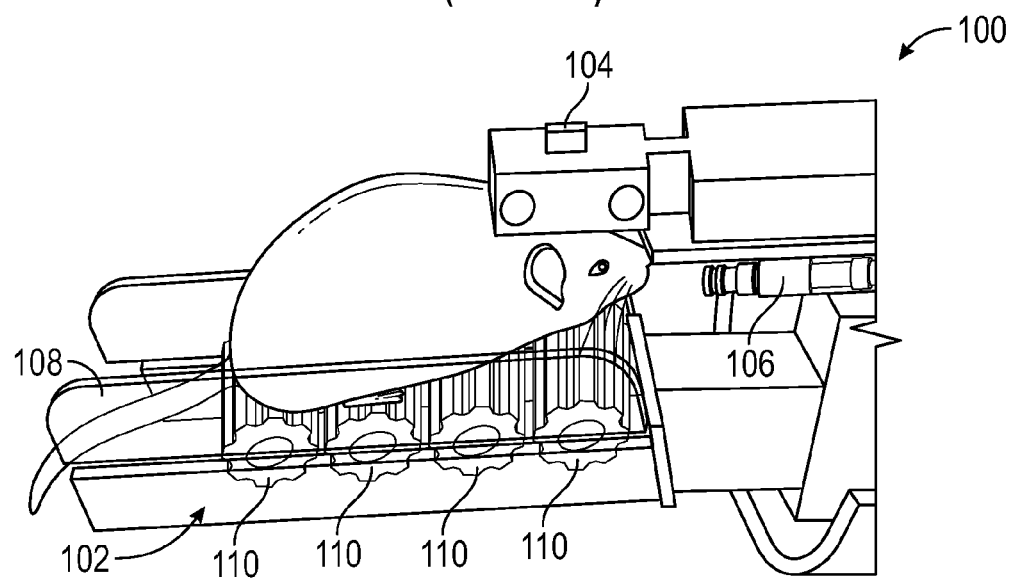
FIG. 2 is a picture showing one embodiment of a system and method for training and imaging an animal operatively associated with a treadmill and head post arrangement having a radio frequency receiver coil.
Figure 3:
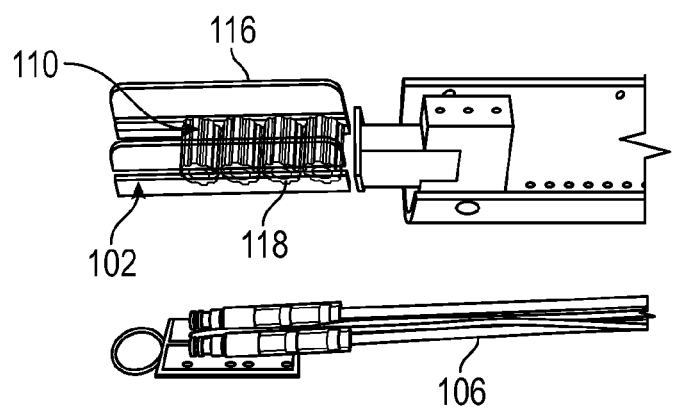
FIG. 3 is a picture showing the radio frequency receiver coil.

As shown in FIGS. 2 and 3, the imaging system 100 includes a stationary head post 104 having one portion attached to the frame 108 and another portion implanted within the skull of the rodent to maintain the head of the rodent in substantially the same position relative to the frame 108 as shall be discussed below. In addition, a radio frequency receiver coil 106 for receiving signals from the rodent during imaging within the imaging apparatus 114 (FIG. 5) is positioned along the head post 104 proximate the rodent. In some embodiments, the frame 108 may include a pair of opposing side walls 116 and 118 to confine the rodent within the enclosure defined by the frame 108 as shown in FIG. 3.

In operation, the rodent is trained to maintain its head substantially still during imaging by either remaining motionless within the frame 108 or by walking on the plurality of rollers 110 on the treadmill 102 when in motion, which permits the rodent's head to maintain a substantially still position relative to the radio frequency receiver coil 106. As such, the fixation of the rodent's head to the head post 104 over time trains the rodent to walk on the treadmill 102 when in motion within the frame 108. After training, stress related associated with an imaging procedure is minimized.

As noted above, the plurality of rollers 110 are rotated by the walking motion of the rodent alone on the treadmill 102 and do not require an electric motor to cause the plurality of rollers 110 to rotate. Accordingly, the rodent can walk on the treadmill 102 at its own pace if it chooses to walk, while the plurality of rollers 110 stops rotating anytime the rodent ceases to walk.

Figure 4:
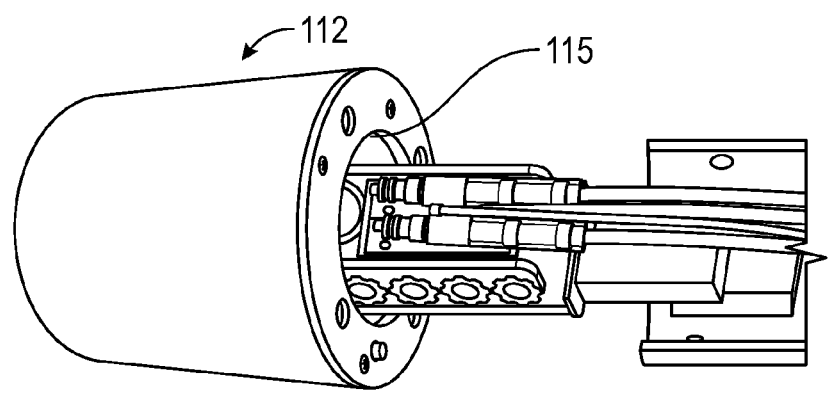
FIG. 4 is a picture showing a radio frequency transmitter coil.
Figure 5:
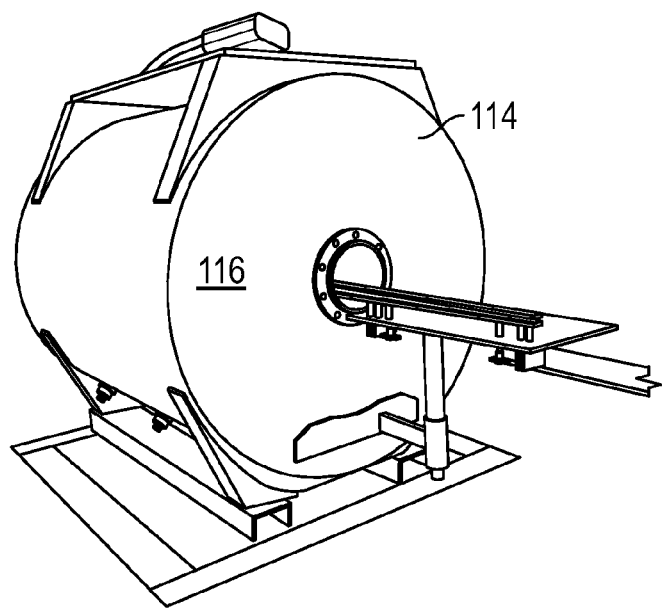
FIG. 5 is a picture showing one embodiment of an imaging apparatus for imaging the animal.

Referring to FIG. 4, the frame 108 with the head post 104 attached to the rodent and the treadmill 102 is then housed within an enclosure 115 defined by the radio frequency transmitter coil 112. The radio frequency transmitter coil 112 may then be disposed within a magnet 116 of the imaging apparatus 114 as shown in FIG. 5 so that the awaken rodent may be imaged while remaining substantially still within the frame 108 as discussed above.

During experiments using the imaging system 100, the trained rodents got used to the fixation of the head to the head post 104 since body restraint stress is minimized, thereby dramatically increasing the imaging success rate of the rodent in the awaken state.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. An animal imaging and training system comprising:
    a frame defining an enclosure;
    a treadmill forming a portion of the frame, the treadmill having a plurality of rollers, wherein the plurality of rollers rotate when an animal is in a walking motion on the treadmill and wherein the plurality of rollers do not rotate when the animal ceases to be in a walking motion;
    a head post having a first portion attached to the frame and a second portion attached to the animal;
    a radio frequency receiver coil attached to the frame and in proximity to the animal for detecting radio frequency signals;
    a radio frequency transmitter coil operatively associated with the frame; and
    an imaging apparatus for housing the radio frequency transmitter coil.

2. The animal imaging and training system of claim 1, wherein the radio frequency transmitter coil includes a casing configured to receive the frame therein for disposing the frame and animal within the imaging apparatus during imaging of the animal.

3. The animal imaging and training system of claim 1, wherein the head post is implanted to the skull of the animal.

4. The animal imaging and training system of claim 1, further comprising:
    a magnet operatively associated with the imaging apparatus for generating an oscillating magnetic field that produces an image of the animal within the frame.

5. The animal imaging and training system of claim 4, wherein the imaging apparatus comprises a Magnetic Resonance Imaging Apparatus, a Computer Tomography Apparatus, and a Positron Emission Tomography Apparatus.

6. The animal imaging and training system of claim 1, wherein the treadmill forms a lower portion of the frame.

7. The animal imaging and training system of claim 1, wherein the frame includes a pair of opposing side walls that collectively define the enclosure.

8. The animal imaging and imaging system of claim 1, wherein the head post is located above the treadmill.

9. A method for training and imaging an animal comprising:
    providing an animal imaging system comprising:
        a frame defining an enclosure;
        a treadmill forming a portion of the frame, the treadmill having a plurality of rollers;
        a head post having a first portion attached to the frame;
        a radio frequency receiver coil attached to the frame and in proximity to the animal within the frame for detecting radio frequency signals;
        a radio frequency transmitter coil operatively associated with the frame for transmitting the radio frequency signals; and
        a magnet for housing the radio frequency transmitter coil;
    positioning the animal within the enclosure defined by the frame such that the animal is in operative connect with the plurality of rollers of the treadmill; and
    allowing the animal to walk on the plurality of rollers of the treadmill when the animal is in motion.

10. The method of claim 9, further comprising:
    attaching a second portion of the head post to the animal.

11. The method of claim 10, wherein attaching the second portion of the head post to the animal comprises implanting the second portion of the head post to the skull of the animal.

12. The method of claim 9, further comprising:
    allowing one or more of the plurality of rollers to rotate when the animal is walking on the treadmill and allowing the one or more plurality of rollers to stop rotating when the animal is not walking on the treadmill.

13. The method of claim 9, wherein the second portion of the head post maintains the animal's head in a substantially motionless state.

14. The method of claim 12, wherein rotation of the one or more plurality of rollers causes the animal to be maintained in substantially same position along the treadmill.

15. The method of claim 1, further comprising:
    disengaging the second portion of the head post from the animal after a predetermined period of time.

* * * * *